(12) United States Patent
Chen

(10) Patent No.: US 8,828,903 B2
(45) Date of Patent: Sep. 9, 2014

(54) COPPER CATALYST FOR DEHYDROGENATION APPLICATION

(75) Inventor: Jianping Chen, Hudson, OH (US)

(73) Assignee: BASF Corporation, Florham Park, NJ (US)

( * ) Notice: Subject to any disclaimer, the term of this patent is extended or adjusted under 35 U.S.C. 154(b) by 677 days.

(21) Appl. No.: 12/424,014

(22) Filed: Apr. 15, 2009

(65) Prior Publication Data

US 2010/0121080 A1    May 13, 2010

Related U.S. Application Data

(60) Provisional application No. 61/113,125, filed on Nov. 10, 2008.

(51) Int. Cl.
| | | |
|---|---|---|
| *C07D 307/02* | (2006.01) | |
| *B01J 35/10* | (2006.01) | |
| *B01J 37/00* | (2006.01) | |
| *B01J 23/889* | (2006.01) | |
| *C07D 307/33* | (2006.01) | |
| *B01J 37/03* | (2006.01) | |

(52) U.S. Cl.
CPC ........... *B01J 23/8892* (2013.01); *B01J 35/108* (2013.01); *B01J 37/0009* (2013.01); *C07D 307/33* (2013.01); *B01J 37/03* (2013.01)
USPC ........... 502/244; 502/102; 502/234; 502/240; 502/241

(58) Field of Classification Search
USPC .................................. 502/300, 346, 348, 355
See application file for complete search history.

(56) References Cited

U.S. PATENT DOCUMENTS

| | | | |
|---|---|---|---|
| 5,124,295 A | 6/1992 | Nebesh et al. | |
| 5,134,108 A | 7/1992 | Thakur et al. | |
| 5,210,229 A | 5/1993 | Ichiki et al. | |
| 5,243,095 A * | 9/1993 | Roberts et al. | 568/864 |
| 5,245,095 A * | 9/1993 | Graves et al. | 585/351 |
| 5,981,769 A | 11/1999 | Baur et al. | |
| 6,093,677 A | 7/2000 | Mercker et al. | |
| 6,455,464 B1 * | 9/2002 | Chen | 502/346 |
| 6,903,050 B2 | 6/2005 | Ilinich et al. | |
| 6,916,457 B2 | 7/2005 | Chen | |
| 6,992,037 B2 | 1/2006 | Chen et al. | |
| 7,807,603 B2 * | 10/2010 | Schlitter et al. | 502/346 |

FOREIGN PATENT DOCUMENTS

WO    WO2005058491    *    6/2005

* cited by examiner

*Primary Examiner* — Melvin C Mayes
*Assistant Examiner* — Colette Nguyen
(74) *Attorney, Agent, or Firm* — Melanie L. Brown

(57) ABSTRACT

Disclosed are catalytic compositions having from about 35% to about 75% of Cu by weight, from about 15% to about 35% of Al by weight, and about 5% to about 20% of Mn by weight. The catalytic compositions are bulk homogeneous compositions formed from extruding and calcinating a powder formed from a precipitation reaction of $Cu(NO_3)_2$, $Mn(NO_3)_2$, $Na_2Al_2O_3$. The catalytic compositions have one or more crystalline phases of one or more of CuO and $Cu_xMn_{(3-x)}O_4$, where x is from about 1 to about 1.5, or both. The catalytic compositions are useful for the conversion of 1,4-butane-diol to γ-butyrolactone by a dehydrogenation reaction.

18 Claims, 8 Drawing Sheets

COPPER CATALYST FOR DEHYDROGENATION APPLICATION

CROSS-REFERENCE TO RELATED APPLICATIONS

This application claims the benefit of priority to Provisional Application Ser. No. 61/113,125 filed on Nov. 10, 2008, which is incorporated herein by reference.

TECHNICAL FIELD

This disclosure relates to $CuO/MnO_2/Al_2O_3$ catalysts useful for the dehydrogenation of 1,4-butanediol to γ-butyrolactone and methods of making and using the same.

BACKGROUND

The synthesis of many industrial chemicals only proceeds at an appreciable kinetic rate in the present of a catalyst as a necessary component. When a compound is synthesized by means of a catalyst, the rate of production and, therefore, the cost of production becomes highly dependant upon the catalytic efficiency of the catalyst as well as the cost and longevity of the catalyst. Increased catalytic efficiency allows greater throughput of starting materials over the catalyst while increased longevity of the catalyst reduces equipment downtime and the cost of catalyst materials.

Several catalysts for the conversion of 1,4-butanediol to γ-butyrolactone are known. In a typical application, gas phase 1,4-butanediol is passed over the catalyst at an elevated temperature. Copper metal placed on a porous support allows for catalysis; however, catalytic efficiency is poor and a large amount of byproducts are produced. Catalysts based upon Cu/Cr/Mn, Cu/Cr/Zn, and Cu/Cr contain toxic Cr, are difficult to prepare, and potentially environmentally hazardous. CuO catalyst are formed from less toxic materials, but still have catalytic efficiency and longevity that fall below levels that allow for synthesis of γ-butyrolactone with optimal efficiency.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The catalytic compositions and methods disclosed herein provide for increased throughput of starting material to product and decreased deactivation rates for the dehydrogenation of 1,4-butane-di-ol to γ-butyrolactone. The catalytic compositions contain $CuO/MnO_2/Al_2O_3$ mixture formed by a precipitation reaction followed by extrusion and calcination. The disclosed catalysts are remarkable in comprising a high fraction of CuO or other copper oxide by weight. Specifically, the disclosed catalysts contain from about 35% to about 75% by weight Cu.

One aspect of the invention is directed toward a catalytic composition having from about 35% to about 75% by weight of Cu, from about 15% to about 35% by weight of Al, and from about 5% to about 20% by weight of Mn.

Another aspect of the invention is directed toward a catalytic composition having from about 35% to about 75% of Cu by weight, from about 15% to about 35% of Al by weight, and from about 5% to about 20% of Mn by weight, where the catalytic composition is a bulk homogeneous composition formed by extruding and calcination.

Yet another aspect of the invention is directed toward a method for making a copper catalyst by co-precipitating a solid catalyst composition from solutions containing a soluble copper salt, a soluble manganese salt, and a soluble aluminum compound at a pH of about at about 6 to about 8.5; and calcining the solid catalyst composition under air from about 400 to about 700° C. for a time period from about 2 to about 5 hours.

Still yet another aspect of the invention is directed toward a process for converting 1,4-butane-di-ol to γ-butyrolactone by using a catalytic composition containing from about 35% to about 75% by weight Cu, from about 15% to about 35% by weight Al, and from about 5% to about 20% by weight Mn.

DETAILED DESCRIPTION

Figure 1:
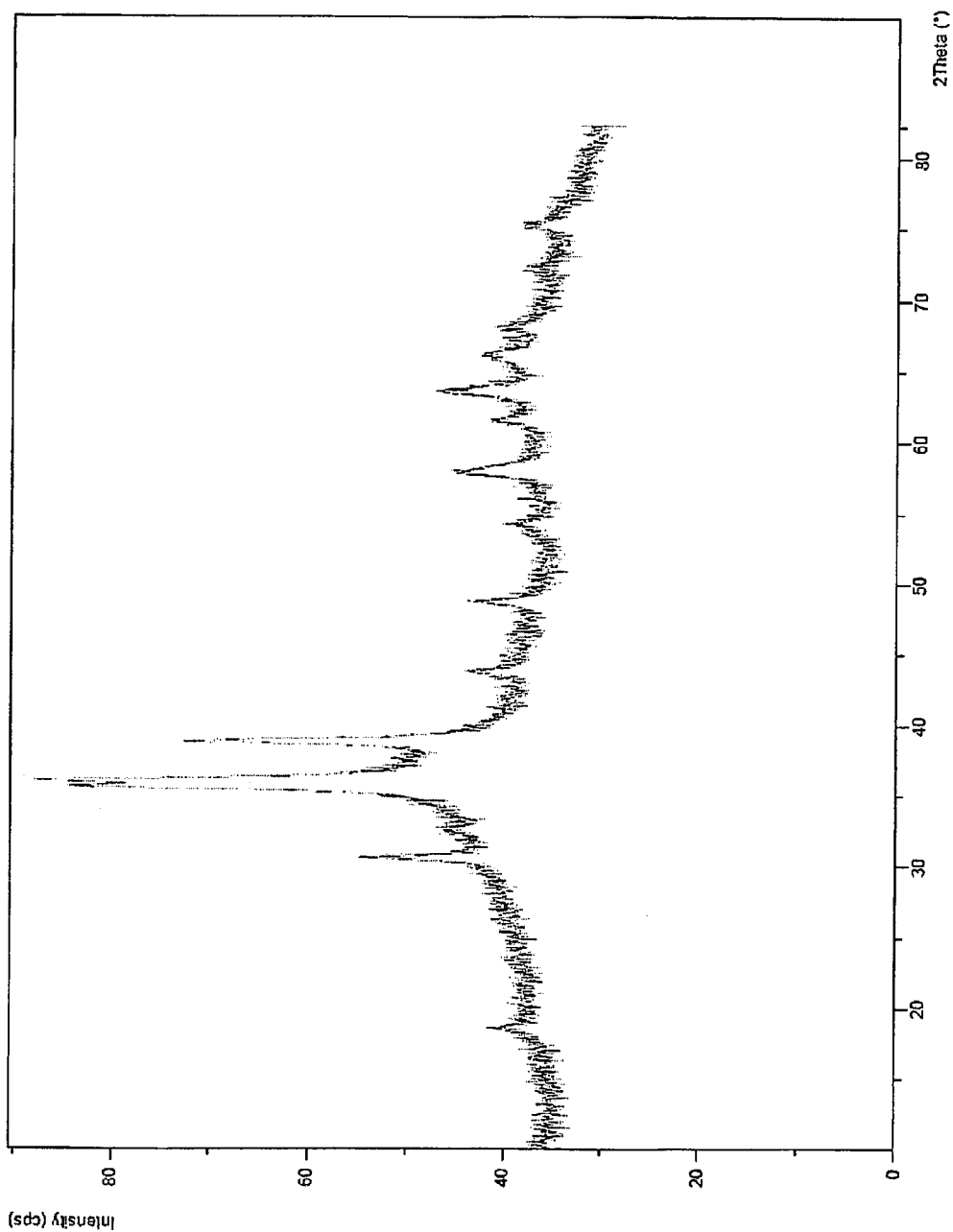
FIG. 1 depicts x-ray diffraction data (Cu Kα source radiation) collected from a catalytic composition in accordance with one aspect of the invention.

The innovations discussed herein are directed toward a $CuO/MnO_2/Al_2O_3$ composition (catalytic composition) useful for the catalyzed dehydrogenation of 1,4-butane-di-ol (BDO) to γ-butyrolactone (GBL) and hydrogen gas. The composition is also potentially useful in other systems that use a copper-based catalyst to increase reaction rate. After an activation period where catalytic activity may increase, most catalysts exhibit a decrease in catalytic activity overtime. Deactivation of a catalyst necessitates costly replacement due to both downtime of equipment and the cost of expensive catalyst materials. The inventive catalysts are remarkable for having a lower deactivation rate compared to known copper-based catalysts for BDO to GBL reactions. Even more remarkable, the inventive catalysts exhibit catalytic constants several fold higher than known Cu-based catalysts, allowing for higher load rate of reactants onto the catalyst.

The inventive catalyst disclosed herein is a $CuO/MnO_2/Al_2O_3$ catalyst (inventive catalyst) made by co-precipitation of a soluble copper compound, a soluble manganese compound, and a soluble aluminum compound to yield the inventive catalyst in a powder form. The inventive catalyst is employed as a homogeneous bulk composition and not absorbed or contacted with an inert support. The inventive catalyst is extruded, with or without lubricants or binders, to form a solid (non-particulate) catalyst over which BDO is passed. Typically, the inventive catalyst is calcined at about 350 to about 750° C. both after precipitation and after extrusion to solid form.

The empirical formula of the inventive comprises at least about 40% by weight of CuO or other copper oxide. In one embodiment, the inventive catalyst contains from about 35% to about 70% by weight of Cu, optionally as CuO. In another embodiment, the inventive catalyst contains from about 40% to about 65% by weight of Cu, optionally as CuO. In yet another embodiment, the inventive catalyst contains from about 50% to about 60% by weight of Cu, optionally as CuO.

In one embodiment, the inventive catalyst contains from about 15% to about 35% by weight of Al, optionally as $Al_2O_3$. In another embodiment, the inventive catalyst contains from about 20% to about 35% by weight of Al, optionally as $Al_2O_3$. In one embodiment, the inventive catalyst contains from about 5% to about 20% by weight of Mn, optionally as $MnO_2$. In one embodiment, the inventive catalyst contains from about 10% to about 25% by weight of Mn, optionally as $MnO_2$.

Calcination of the inventive catalyst results in the crystallization of at least a portion of the bulk homogeneous catalyst and the formation of at least one crystalline phase detectable by x-ray diffraction, as well as increased mechanical strength. The crystalline phase can have the empirical formula CuO and/or the crystalline phase can have the empirical formula $Cu_xMn_{(3-x)}O_4$, where x is from about 1 to about 1.5. In one embodiment, the inventive catalyst contains both CuO and $Cu_xMn_{(3-x)}O_4$ phases. In another embodiment, the inventive catalyst contains two or more separate $Cu_xMn_{(3-x)}O_4$ phases, each of which can have a separate crystalline phase or twined crystalline phase.

As used throughout this disclosure, the term "by weight" and all references to a metal or metal ion comprising a percentage by weight is herein defined as the mass of the referenced metal or metal ion divided by the weight of the catalyst composition where the weight of the metal or metal ion does not include the weight of any counter ions. A recitation that a catalytic composition contains or comprises a weight percent of metal includes catalytic composition containing or comprising that weight percentage of a corresponding metal ion. The terms "bulk homogeneous catalyst" and "bulk homogeneous extrudate" refers to a catalytic composition that is competent to carry out catalysis, as described herein, that consists essentially only of copper, manganese, and aluminum bound with counter ions and optionally binders and/or lubricants such that the components comprising such catalytic composition as homogeneously distributed on a macroscopic scale, where the catalytic composition is not absorbed onto nor contacted with an inert catalytic support.

Preparation of $CuO/Mn_2O/Al_2O_3$ Catalyst

The catalytic compositions disclosed herein are formed from recovering a solid precipitate by co-precipitating a solid catalyst composition from solutions containing a soluble copper salt, a soluble manganese salt, and a soluble aluminum compound at a pH from about 6 to about 8.5. The recovered solid catalyst composition is calcined under air from about 400 to about 700° C. for a time period from about 2 to about 5 hours before use as a catalyst. In one embodiment, the co-precipitation is done from solutions of copper (II) nitrate, manganese (II) nitrate, and sodium aluminate. Separate copper (II) nitrate and manganese (II) nitrate solutions are combined to form a single solution, and the combined copper (II) nitrate and manganese (II) nitrate solution and an aluminate solution are then combined by addition to an aqueous media over a predetermined time period. In embodiment, the predetermined time period is from about 40 to about 80 minutes. The precipitation reaction is performed with a base to maintain pH within a desire range. In one embodiment, the aqueous media to which the copper (II) nitrate, manganese (II) nitrate, aluminate, and base solutions are added is water, deionized water, or substantially comprised of water.

In another embodiment, the soluble copper salt is one or more selected from copper (II) acetate, copper (II) chloride, copper (II) nitrate, and copper (II) sulfate. In another embodiment, the soluble manganese salt is one or more selected from manganese (II) sulfate, manganese (II) chloride, manganese (II) bromide, and manganese (II) nitrate.

The base used to titrate the aqueous media of the precipitation reaction contains from about 1 to about 2 mole equivalents of base per liter. In one embodiment, the base added to maintain pH in a desired range is sodium carbonate. Since the carbonate ion is dibasic, a carbonate solution that is from about 0.5 to about 1 mole per liter of sodium carbonate contains from about 1 to about 2 mole equivalents of base per liter. In one embodiment, the base is added such that the pH of the aqueous media of the precipitation reaction is maintained at about 6 to about 8.5. In another embodiment, the base is added such that the pH of the aqueous media of the precipitation reaction is maintained at about 6.5 to about 8. In yet another embodiment, the base is added such that the pH of the aqueous media of the precipitation reaction is maintained at about 6.5 to about 7.5.

In one embodiment, the catalytic composition is prepared by forming a combined $Cu(NO_3)_2$ and $Mn(NO_3)_2$ solution from separate $Cu(NO_3)_2$ and $Mn(NO_3)_2$ aqueous solutions. The combined solution has a concentration of $Cu(NO_3)_2$ from about 1 to about 3.3 moles per liter, a concentration of $Mn(NO_3)_2$ from about 0.3 to about 1 mole per liter, and a concentration of nitric acid ($HNO_3$) from about 0.25 to about 1% by weight of the solution. The nitric acid component is originally a component of the separate $Cu(NO_3)_2$ solution. The precise compositions of the separate $Cu(NO_3)_2$ and $Mn(NO_3)_2$ solutions are not critical provided that the combined solution has the required concentration of components. Those skilled in the art will readily understand that a catalytic composition can be formed by a precipitation reaction using a soluble copper, soluble manganese, and base solutions having different concentrations than described above. The above recited concentrations are only examples of concentrations used for a typical precipitation reaction.

The aluminate solution comprises $Na_2Al_2O_4$ dissolved in a media sodium hydroxide and water with a pH of about 12 or higher at a concentration from about 0.2 to about 0.4 kg of $Na_2Al_2O_4$ per liter (about 1.2 to about 2.4 mol $l^{-1}$). Those skilled in the art recognized that $Na_2Al_2O_4$ in basic solution can break down into $Al_2O_3$ and $Na_2O$. Concentrations for sodium aluminate solutions are calculated by the total weight of $Na_2Al_2O_4$, $Al_2O_3$ and $Na_2O$ in solution converted into the stoichiometric equivalent of $Na_2Al_2O_4$. An aluminate solution is sold commercially as USALCO 45 (US Aluminum Co., Baltimore, Md.), which is 45% $Na_2Al_2O_4$ by weight, and can be diluted to form a useful aluminate solution. Those skilled in the art will readily understand that a catalytic composition can be formed by a precipitation reaction using a soluble aluminum solution having a different concentration than described above. The above recited concentrations are only an examples of concentrations used for a typical precipitation reaction.

The combined $Cu(NO_3)_2$ and $Mn(NO_3)_2$ solution, the aluminate solution and the base for pH titration are added to an aqueous media, as described above, where the precipitation reaction occurs. The volume of the aqueous media is from about 4 to about 7 times the volume of the combined $Cu(NO_3)_2$ and $Mn(NO_3)_2$ solution to be used. The volume of combined $Cu(NO_3)_2$ and $Mn(NO_3)_2$ solution to be used is determinative of the amount of catalytic composition to be synthesized and the volume of the aqueous media is adjusted accordingly. In one embodiment, the combined $Cu(NO_3)_2$ and $Mn(NO_3)_2$ solution is added a rate such that the entire of volume of the combined $Cu(NO_3)_2$ and $Mn(NO_3)_2$ solution to be used is added to the aqueous media over a time period from about 40 to about 80 minutes. In another embodiment, the combined $Cu(NO_3)_2$ and $Mn(NO_3)_2$ solution is added a rate such that the entire of volume of the combined $Cu(NO_3)_2$ and $Mn(NO_3)_2$ solution to be used is added to the aqueous media over a time period from about 50 to about 70 minutes.

The aluminate aqueous solution is added to the aqueous media at a rate of volume per unit time that is approximately about 65% to about 100% of the rate of volume per unit time of the addition of the combined $Cu(NO_3)_2$ and $Mn(NO_3)_2$ solution. In another embodiment, the volume of aluminate solution is easily calculated to achieve a desired distribution of $CuO/MnO_2/Al_2O_3$ within the catalytic composition, as described above, and the known concentration of the $Cu(NO_3)_2$ and $Mn(NO_3)_2$ solution. In one embodiment, the aluminate aqueous solution is added to the aqueous media over the time period the combined $Cu(NO_3)_2$ and $Mn(NO_3)_2$ solution is added to the aqueous media, as described above. In yet another embodiment, the aluminate aqueous solution is added to the aqueous media over a time period that is within about 25% of the time period over which the combined $Cu(NO_3)_2$ and $Mn(NO_3)_2$ solution is added to the aqueous media.

An example of the inventive $CuO/Mn_2O/Al_2O_3$ catalyst prepared through a precipitation reaction is as follows:
Prepare an aqueous solution of $Cu(NO_3)_2$ to be 16.2% by weight Cu (31.5% by weight $Cu(NO_3)_2$) and 0.823% by weight nitric acid; measure 8.575 Kg of the prepared $Cu(NO_3)_2$ solution. Prepare an aqueous $Mn(NO_3)_2$ solution to be 13.2% by weight Mn (42.9% by weight $Mn(NO_3)_2$). To the described $Cu(NO_3)_2$ solution, add 1.727 Kg of the prepared $Mn(NO_3)_2$ solution to form the combined $Cu(NO_3)_2$ and $Mn(NO_3)_2$). After mixing, the volume of the new combined $Cu(NO_3)_2$ and $Mn(NO_3)_2$ solution is approximately 6650 ml, the molarity of $Cu(NO_3)_2$ is about 2.19 mol $l^{-1}$, and the molarity of $Mn(NO_3)_2$ is about 0.623 mol $l^{-1}$. Prepare an aqueous solution of sodium aluminate by measuring 3.586 kg of USALCO 45 solution (US Aluminum Co., Baltimore, Md.) and dilute to 5450 ml with deionized water; the final aluminate solution is 29.5% by weight of dissolved sodium aluminate (about 1.81 mol $l^{-1}$ of $Na_2Al_2O_4$). Finally, prepare a solution of sodium carbonate (soda ash) by dissolving 1906.9 g of sodium carbonate in 21.8 l of deionized water (about 0.825 mol $l^{-1}$). Deionized water is used to make all solutions.

The inventive catalyst is prepared adding the combined $Cu(NO_3)_2$ and $Mn(NO_3)_2$ solution, the sodium aluminate solution and the sodium carbonate solution to 38 l of deionized water as the aqueous media. The $Cu(NO_3)_2$ and $Mn(NO_3)_2$ solution is added at a rate of approximately 111 ml/min and the sodium aluminate solution is added at a rate of approximately 91 ml/min. The soda ash solution is added at a rate to keep the pH of the precipitation reaction at about a pH of 7.

The precipitation can be successfully carried out over a wide range of temperature from room temperature to about boiling. The example precipitation is performed at about 25° C. During the precipitation, slurry samples can be taken at intervals (approximately every 5 or 10 minutes) and particle size analysis performed thereon. When the precipitation reaction is completed, the slurry is allowed to sit until a stable pH is reached. The slurry should be filtered to remove bulk solution, and the filter cake washed until the conductivity of eluting filtrate is less than 1 microohms/cm. The cake comprising the inventive catalytic composition should then be weighed and placed in a drying oven at about 150° C. for approximately 8 to 10 hours. If desired, the loss on drying (LOD) may be recorded after the cake comprising the inventive catalyst is removed from the drying oven. The dried catalyst cake can be optionally calcined from about 400 to about 700° C. at this point.

A powder is recovered from the dried cake. Chemical analysis determined the resulting powder to contain 54.4% by weight Cu as CuO, 8.32% by weight Mn as $MnO_2$, and 26% by weight Al as $Al_2O_3$.

The catalyst is employed in the form of a bulk homogeneous extrudate, which can be formed with or without lubricants or binders. When lubricants and binders are not used, the dried catalyst cake is recovered in the form of a powder at combined with deionized water. The amount of water added is such that a weight loss upon drying from about 30% to about 42% will be achieved when water is removed. That is, water is added to form a mixture of catalytic composition and water, where water comprises about 30% to about 42% of the mixture. The mixture is mixed in a mixer until a densification occurs, where the catalyst will form firm individual spheres. A usable catalyst is then recovered by extrusion and required calcination under air from about 400 to about 700° C.

In cases where binders and lubricants are used, part of the mass of inventive catalyst powder used is replaced with binders and lubricants that are well-known in the art. Examples of binders and lubricants include lime hydrate, amorphous silica, and methylcellulose polymers.

Example 1

Extrudate of Inventive Catalyst

Before extrusion, the inventive catalyst obtained from the above-described procedure is calcined at about 500° C. for about 2 to about 4 hours. In another embodiment, the inventive catalyst is calcined under air from about 400 to about 700° C. for a time period from about 2 to about 5 hours. Deionized water is added to approximately 1000 g of the inventive catalyst powder without any binders or lubricants. The amount of water added is calculated such that the loss of weight upon drying is approximately 30% to about 42%. The mixture of water and inventive catalyst will become dense under mechanical mixing and form spheres of approximately 1/16 inch in diameter. The mixture is mixed at a moderate speed in a mixer.

The densified mixture is extruded through a 2 inch extruder with a set of tri-inserts with a 3/8 inch extrusion forming zone. A continuous and smooth extrudate is formed; the extrudate is dried at about 120° C. for approximately 2 to 3 hours. The extrudate is calcined under air at about 500° C. for approximately 4 hours. The bulk density of the inventive catalyst extrudate is 0.57 g/ml and the extrudate is 1/16 inch in diameter after all processing is complete. Those having skill in the art will recognize that the bulk density of extrudates can vary depending upon composition. In one embodiment, the bulk density of the inventive catalyst extrudate is from about 0.4 to about 0.8 g/ml. In another embodiment, the bulk density of the inventive catalyst extrudate is from about 0.5 to about 0.7 g/ml.

Example 2

Extrudate of Inventive Catalyst

A second example of an inventive catalyst extrudate is formed using the same methods as above, except binders are included in the preparation. The following components are mixed:

2400 g of inventive catalyst from the precipitation reaction described above;

760 g of lime hydrate $Ca(OH)_2$;

1700 g amorphous silica solution (Nalco® 1034A, Nalco Co., Naperville, Ill.); and 40 g water soluble methylcellulose and hydroxypropyl methylcellulose polymer (Methocel®, Dow Chemical).

The amorphous silica is dissolved in water and added to the remaining components. The amount of water used to form the silica solution is calculated such that the loss of weight upon drying of the catalytic composition is approximately 30% to about 42%. The mixture is mixed, extruded and calcinated as above.

Example 3

Extrudate of Inventive Catalyst

A third example of an inventive catalyst extrudate is formed using the same methods as above, except binders are included in the preparation. The following components are mixed:

1400 g of powder inventive catalyst;

1000 g calcium silicate (Celite Corp., Lompoc, Calif.)

760 g of lime hydrate $Ca(OH)_2$;

1700 g amorphous silica solution (Nalco® 1034A, Nalco Co., Naperville, Ill.); and 40 g water soluble methylcellulose and hydroxypropyl methylcellulose polymer (Methocel®, Dow Chemical).

The silica solution is prepared and mixing, extruding, and calcination are performed as above.

X-ray Diffraction Characterization of Example 1

FIG. 1 depicts x-ray diffraction analysis of the Example 1 extrudate of the inventive catalyst.

The peak pattern obtained from powder diffraction was analyzed with using the POWD-12++ program (1997). From the diffraction pattern shown in FIG. 1, a CuO crystalline phase is detected having a monoclinic C2/c space group. The unit cell dimensions assigned are a=4.68 Å, b=3.43 Å, c=5.14 Å, and β=99.3°. In addition, a crystal phase having an empirical formula $Cu_{1.5}Mn_{1.5}O_4$ having a cubic space group Fd-3m. The unit cell length of the cubic space group observed is 8.29 Å. Table 1 lists the hkl indexing, Bragg index, 2θ Bragg angle, and relative intensity for peaks belonging to the CuO crystalline phase. Table 2 lists the hkl indexing, Bragg distance, 2θ Bragg angle, and relative intensity for peaks belonging to the $Cu_{1.5}Mn_{1.5}O_4$ crystal phase.

TABLE 1

Diffraction Peaks Observed for Monoclinic CuO Crystal Phase

| No. | h | k | l | d [Å] | 2θ [deg] | I [%] |
|---|---|---|---|---|---|---|
| 1 | 1 | 1 | 0 | 2.75443 | 32.480 | 5.5 |
| 2 | 0 | 0 | 2 | 2.5346 | 35.385 | 25.8 |
| 3 | 1 | 1 | 1 | 2.52399 | 35.539 | 100.0 |
| 4 | 1 | 1 | 1 | 2.32829 | 38.640 | 44.2 |
| 5 | 2 | 0 | 0 | 2.30934 | 38.970 | 16.4 |
| 6 | 1 | 1 | 2 | 1.96128 | 46.252 | 1.4 |
| 7 | 2 | 0 | 2 | 1.86283 | 48.851 | 19.4 |
| 8 | 1 | 1 | 2 | 1.78185 | 51.228 | 0.9 |
| 9 | 0 | 2 | 0 | 1.71570 | 53.355 | 6.9 |
| 10 | 0 | 2 | 1 | 1.62514 | 56.587 | 0.6 |
| 11 | 2 | 0 | 2 | 1.58478 | 58.164 | 9.6 |
| 12 | 1 | 1 | 3 | 1.50620 | 61.517 | 8.1 |
| 13 | 0 | 2 | 2 | 1.42080 | 65.662 | 9.6 |
| 14 | 3 | 1 | 1 | 1.40790 | 66.340 | 6.0 |
| 15 | 3 | 1 | 0 | 1.40466 | 66.513 | 3.4 |
| 16 | 1 | 1 | 3 | 1.38239 | 67.728 | 8.5 |
| 17 | 2 | 2 | 0 | 1.37721 | 68.017 | 8.9 |
| 18 | 2 | 2 | 1 | 1.36254 | 68.852 | 0.3 |
| 19 | 3 | 1 | 2 | 1.31307 | 71.838 | 0.2 |
| 20 | 3 | 1 | 1 | 1.30523 | 72.337 | 6.3 |
| 21 | 2 | 2 | 1 | 1.29789 | 72.812 | 0.3 |
| 22 | 0 | 0 | 4 | 1.26731 | 74.864 | 3.3 |
| 23 | 2 | 2 | 2 | 1.26200 | 75.234 | 3.6 |
| 24 | 0 | 2 | 3 | 1.20390 | 79.559 | 0.1 |
| 25 | 1 | 1 | 4 | 1.19509 | 80.264 | 1.1 |
| 26 | 3 | 1 | 3 | 1.16776 | 82.545 | 3.7 |
| 27 | 2 | 2 | 2 | 1.16415 | 82.857 | 3.2 |
| 28 | 3 | 1 | 2 | 1.15859 | 83.343 | 0.2 |
| 29 | 4 | 0 | 0 | 1.15467 | 83.690 | 2.1 |
| 30 | 2 | 2 | 3 | 1.12105 | 86.806 | 0.8 |
| 31 | 1 | 1 | 4 | 1.11150 | 87.740 | 0.1 |
| 32 | 1 | 3 | 1 | 1.09343 | 89.575 | 1.4 |

TABLE 2

Diffraction Peaks Observed for Cubic $Cu_{1.5}Mn_{1.5}O_4$ Crystal Phase

| No. | h | k | l | d [Å] | 2θ [deg] | I [%] |
|---|---|---|---|---|---|---|
| 1 | 1 | 1 | 1 | 4.78623 | 18.523 | 10.9 |
| 2 | 2 | 2 | 0 | 2.93096 | 30.474 | 35.9 |
| 3 | 3 | 1 | 1 | 2.49953 | 35.899 | 100 |
| 4 | 2 | 2 | 2 | 2.39312 | 37.553 | 7.6 |
| 5 | 4 | 0 | 0 | 2.07250 | 43.638 | 15.7 |
| 6 | 3 | 3 | 1 | 1.90186 | 47.785 | 0.1 |
| 7 | 4 | 2 | 2 | 1.69219 | 54.157 | 8.5 |
| 8 | 5 | 1 | 1 | 1.59541 | 57.740 | 26.8 |
| 9 | 4 | 4 | 0 | 1.46548 | 63.421 | 29.2 |
| 10 | 5 | 3 | 1 | 1.40127 | 66.695 | 0.6 |
| 11 | 4 | 4 | 2 | 1.38167 | 67.768 | 0.1 |
| 12 | 6 | 2 | 0 | 1.31076 | 71.984 | 2.2 |
| 13 | 5 | 3 | 3 | 1.26421 | 75.080 | 5.3 |
| 14 | 6 | 2 | 2 | 1.24976 | 76.101 | 2.4 |
| 15 | 4 | 4 | 4 | 1.19656 | 80.146 | 1.3 |
| 16 | 5 | 5 | 1 | 1.16083 | 83.146 | 0.4 |
| 17 | 6 | 4 | 2 | 1.10780 | 88.109 | 2.3 |

Mercury Intrusion Characterization of Example 1

Figure 2:
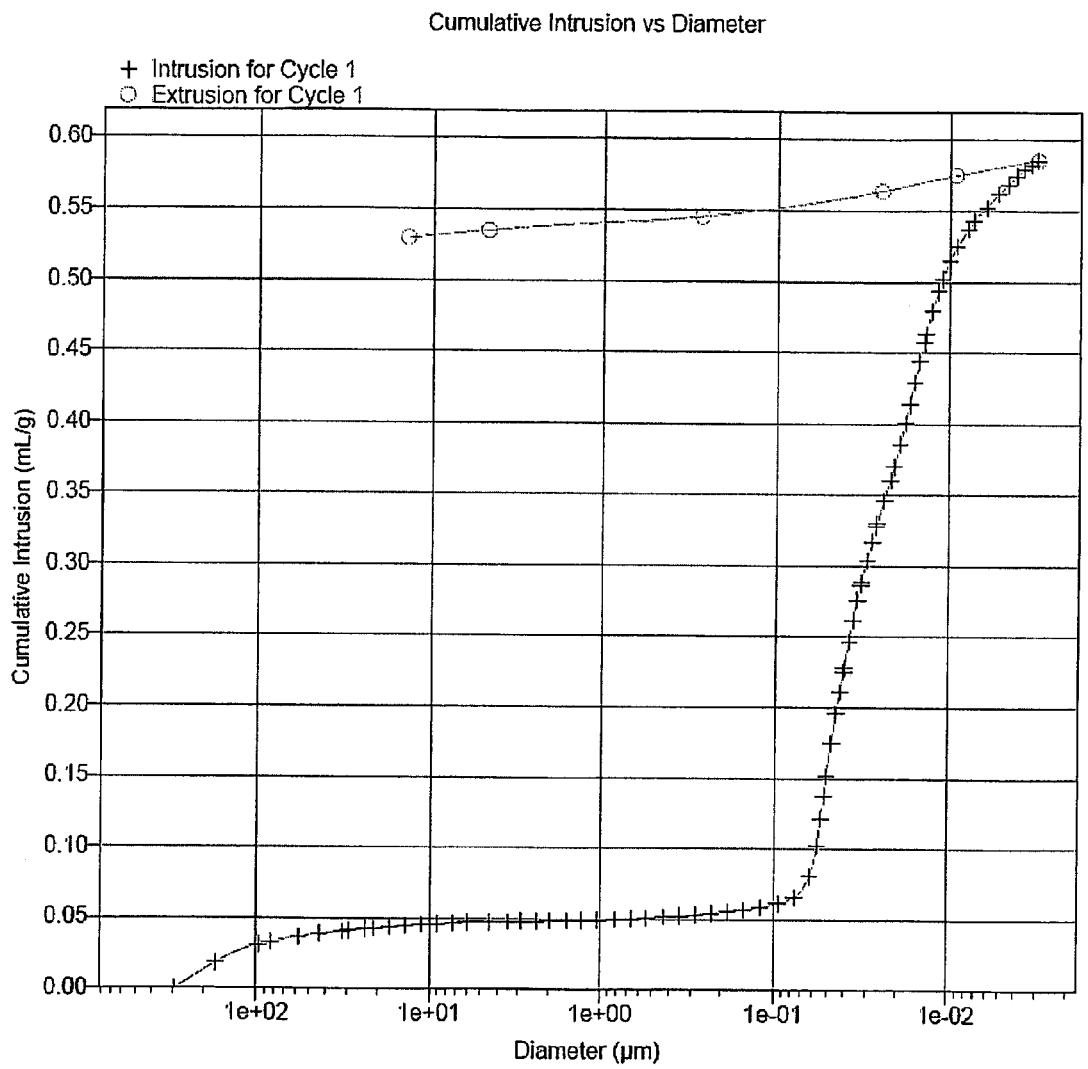
FIG. 2 presents Hg intrusion data collected from a catalytic composition in accordance with one aspect of the invention.
Figure 3:
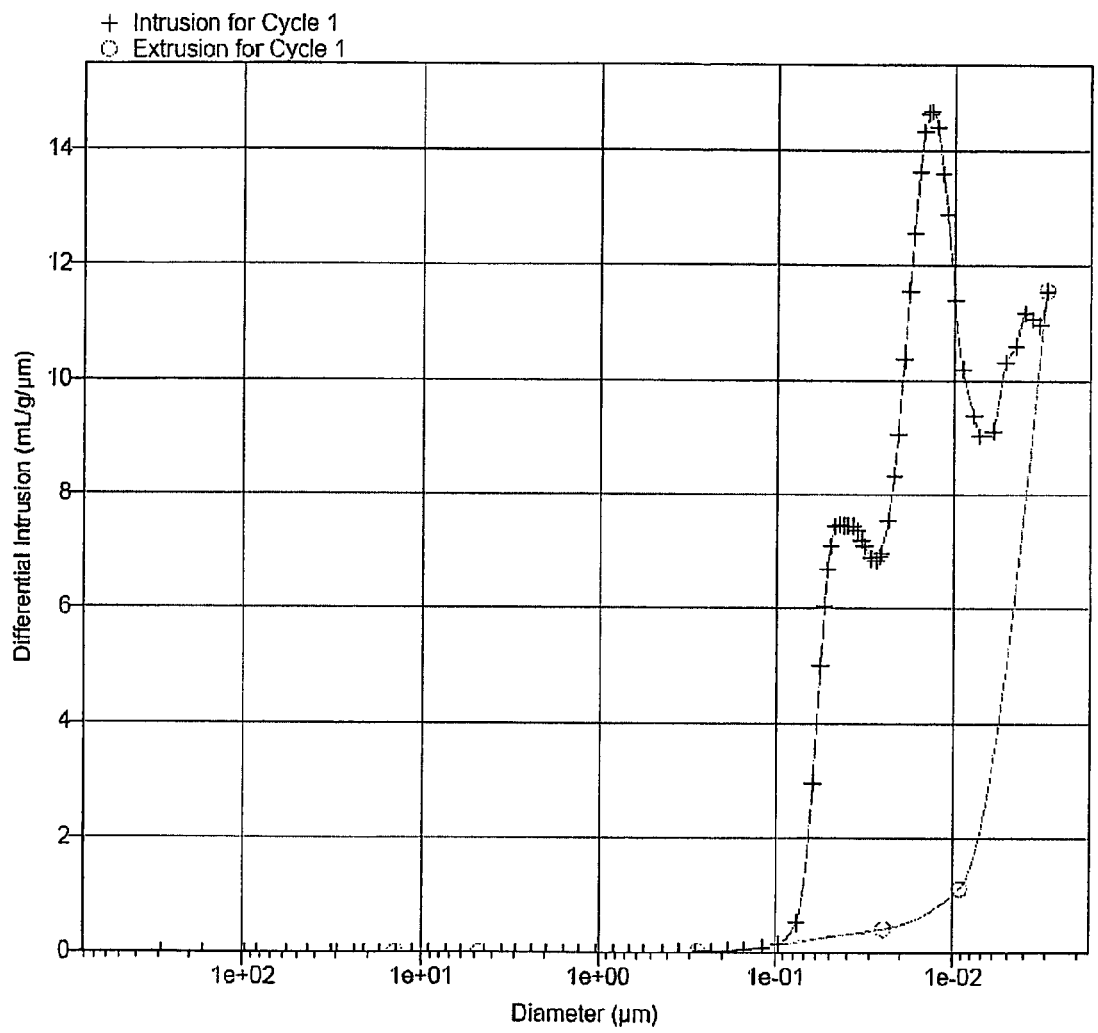
FIG. 3 presents Hg intrusion data collected from a catalytic composition in accordance with one aspect of the invention.

FIGS. 2 and 3 show mercury (Hg) intrusion data for the Example 1 extrudate of the inventive catalyst. FIG. 2 shows total Hg intrusion into the catalyst extrudate in relation to pore size diameter. As can be observed, about 78% of porosity measured by Hg intrusion occurs in pores having a size from 100 Å to 1000 Å. Those having skill in the art will understand that the porosity of catalyst extrudates described herein can vary. In one embodiment, about 75 to about 88% of porosity measured by Hg intrusion occurs in pores having a size from 100 Å to 1000 Å.

FIG. 3 shows the incremental pore size distribution as a function of pore diameter. As can be observed, the pores have a bimodal pore size distribution with local maxima in the pore diameter distribution centered at about 200 Å and about 500 Å, respectively. Since the mean pore diameters are close, the apparent local maxima in pore size distribution from about 200 Å and about 500 Å in diameter may only be an artifact. Since the distribution of pore diameter is close together, those having skill in the art will understand that the porosity of catalyst extrudates described herein can vary. In one embodiment, the pore size distribution of the catalytic extrudates can have at least one mode of distribution having a maximum in pore diameter from about 200 Å to about 1000 Å. In another embodiment, the catalytic extrudates can have a bimodal modal distribution wherein the first local maximum in pore diameter is from about 100 Å to about 350 Å and the second local maximum in pore diameter is from about 250 Å to about 750 Å.

Nitrogen Intrusion Characterization of Example 1

Figure 4:
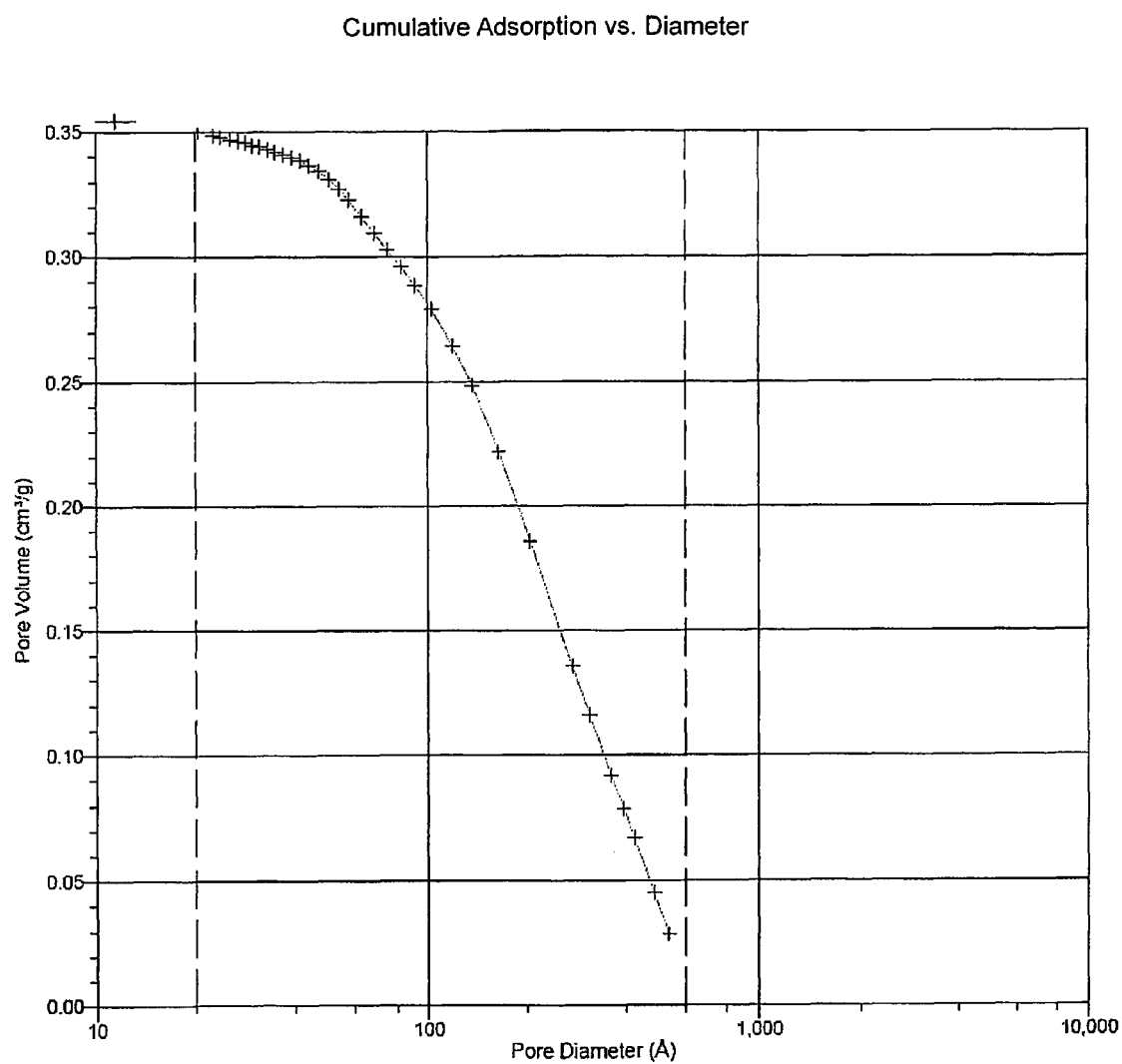
FIG. 4 presents $N_2$ adsorption data collected from a catalytic composition in accordance with one aspect of the invention.
Figure 5:
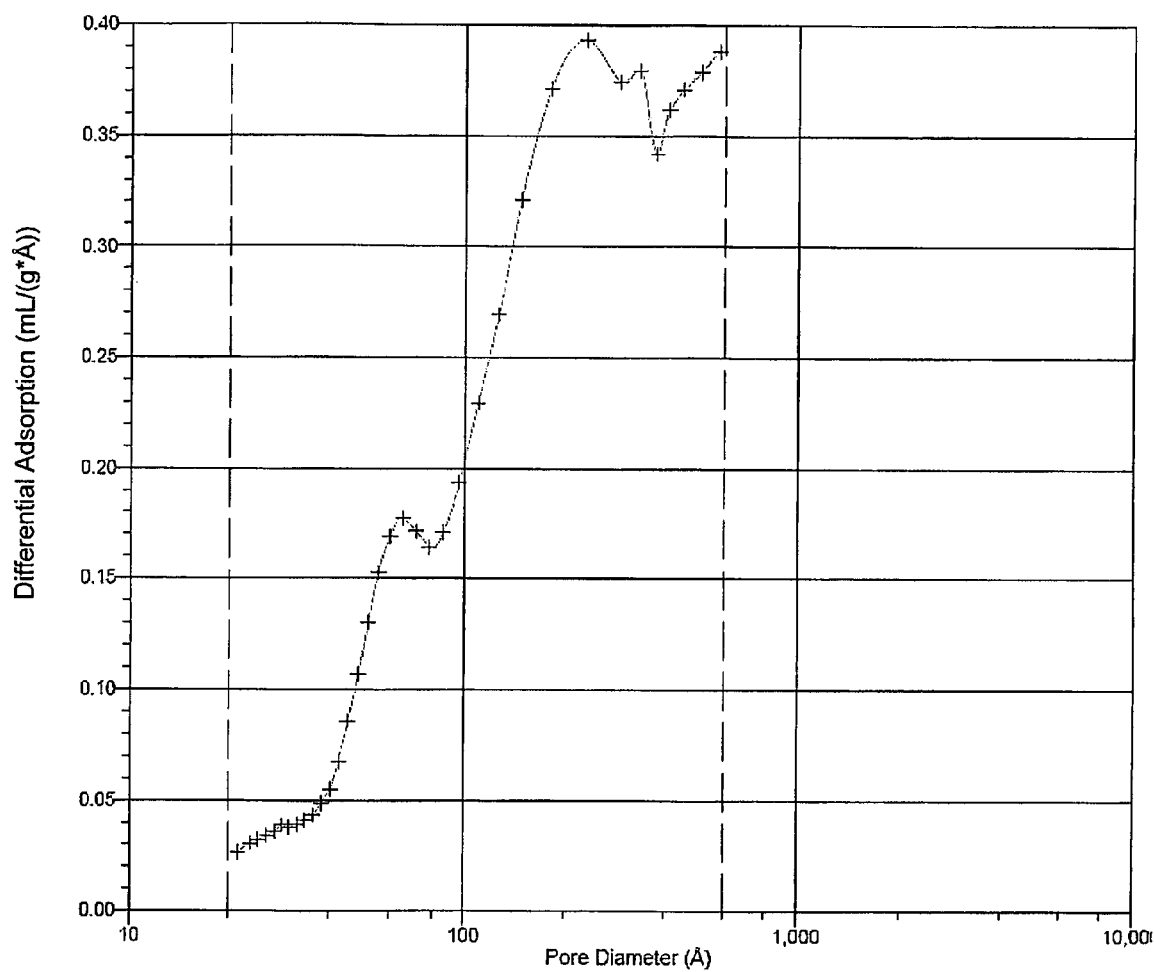
FIG. 5 presents $N_2$ adsorption data collected from a catalytic composition in accordance with one aspect of the invention.

FIGS. 4 and 5 show nitrogen ($N_2$) intrusion data for the Example 1 extrudate of the inventive catalyst. FIG. 4 shows total $N_2$ adsorption into the catalyst extrudate in relation to pore diameter. As can be observed in FIG. 4, about 68% of porosity measured by $N_2$ adsorption occurs in pores having a diameter from 100 Å to 1000 Å. Those having skill in the art will understand that the porosity of catalyst extrudates described herein can vary. In one embodiment, from about 60 to about 88% of porosity measured by $N_2$ adsorption occurs in pores having a diameter from 100 Å to 1000 Å. In another embodiment, from about 60 to about 88% of porosity measured by $N_2$ adsorption occurs in pores having a diameter from 100 Å to 600 Å.

FIG. 5 shows the incremental pore size distribution as a function of pore diameter, as measured by $N_2$ adsorption. As can be observed, the pore size distribution has maximum observed values from about 200 Å to about 500 Å in pore diameter. Those having skill in the art will understand that the porosity of catalyst extrudates described herein can vary. In one embodiment, a maximum in the pore size distribution of catalytic extrudates can be observed from about 100 Å to about 750 Å in diameter. In another embodiment, a maximum in the pore size distribution of catalytic extrudates can be observed from about 200 Å to about 750 Å in diameter.

Hg intrusion and $N_2$ porosity are both methods that measure the porosity of a sample, where values measured by each method can vary due to differences in the respective techniques. Results from both techniques are presented herein for completeness of characterization, where measurements are taken from identical samples of the inventive catalyst.

Differential Scanning Calorimetry of Example 1

Figure 6:
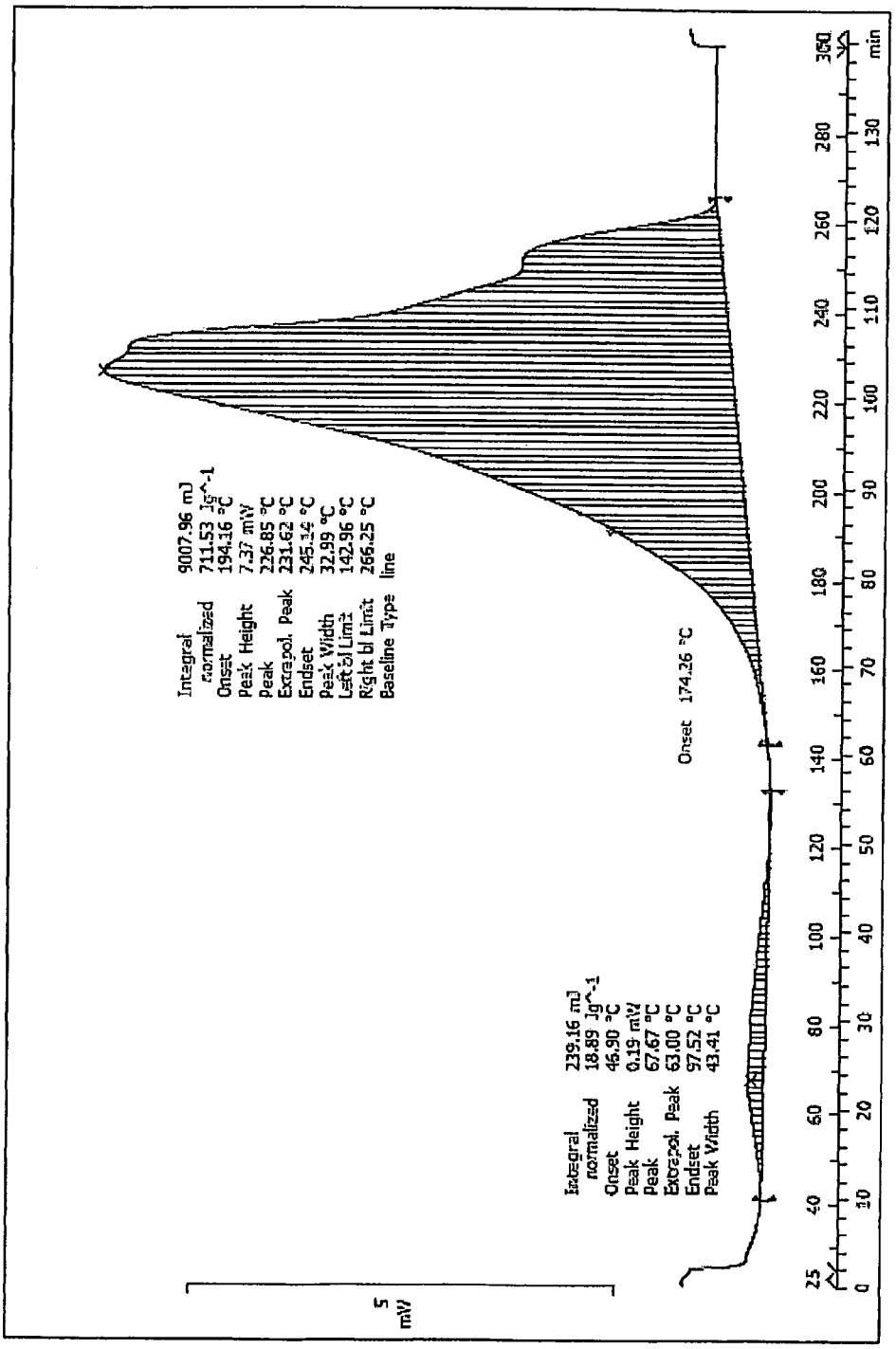
FIG. 6 presents differential scanning calorimetry data collected from a catalytic composition in accordance with one aspect of the invention.

FIG. 6 depicts Differential Scanning Calorimetry (DSC) data collected from the inventive catalyst extrudate of Example 1. The extrudate is heated from 25° C. to 700° C. at a rate of 2° C./min under an atmosphere of 21% hydrogen in argon. As shown in FIG. 6, two large exotherms are observed. The first exotherm is from about 47° C. to about 98° C. with a heat release of about 18.9 J/g. The second exotherm is from about 174° C. to about 254° C. with a heat release of about 711.5 J/g.

Thermal Gravimetric Analysis of Example 1

Figure 7:
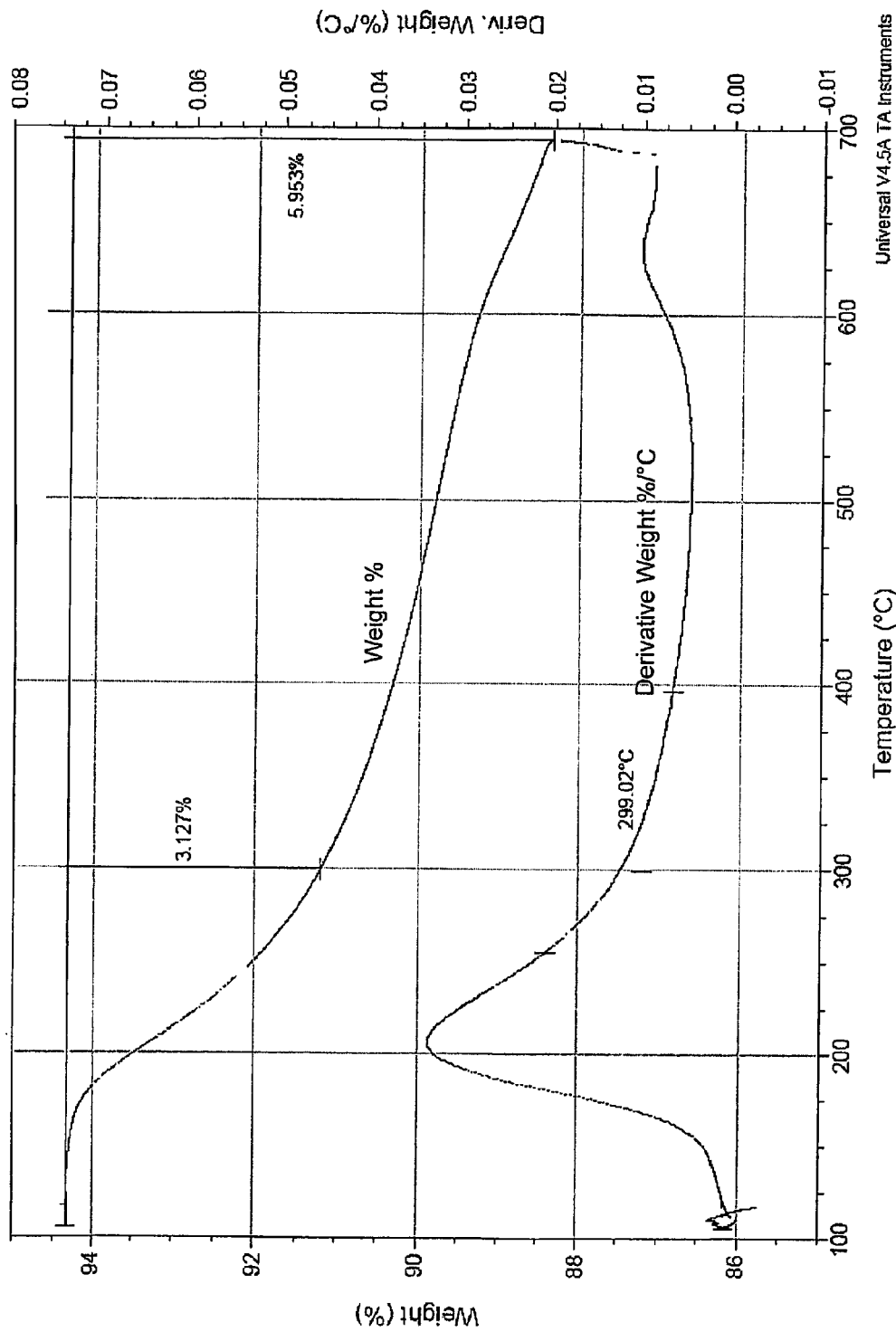
FIG. 7 presents thermal gravimetric analysis data collected from a catalytic composition in accordance with one aspect of the invention.
Figure 8:
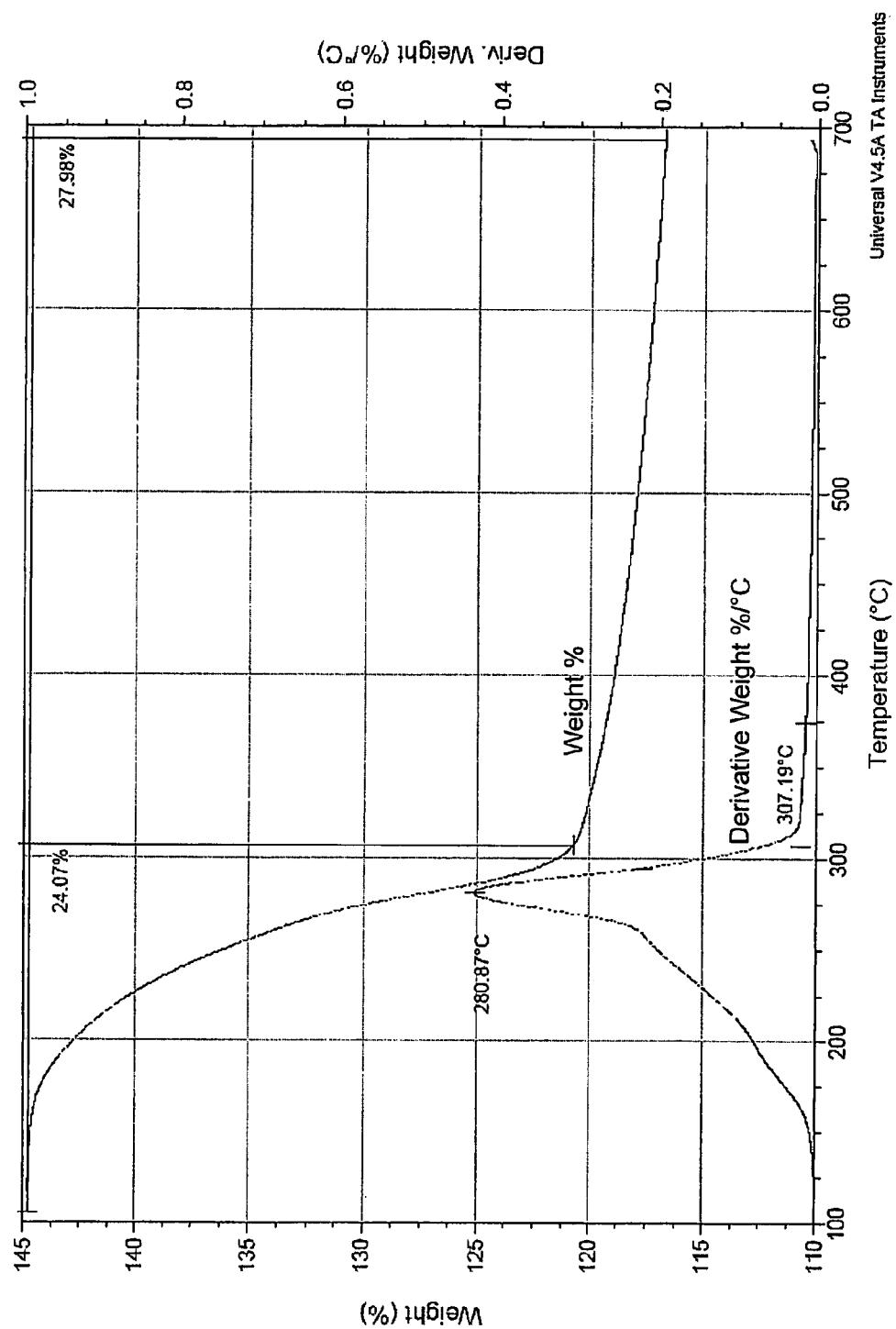
FIG. 8 presents thermal gravimetric analysis data collected from a catalytic composition in accordance with one aspect of the invention.

Thermal Gravimetric Analysis (TGA) data were collected from the inventive catalyst extrudate of Example 1. FIG. 7 presents a plot of the percentage of weight of the sample retained during the heating and a derivative plot of the same for the extrudate of Example 1 under an atmosphere of 21% oxygen in argon. FIG. 8 presents a similar plot for the extrudate of Example 1 under an atmosphere of 10% hydrogen in argon atmosphere. The extrudate is first dried in an argon atmosphere at 150° C. for approximately 30 minutes and then cooled to approximately 100° C. The extrudate is heated from 100° C. to 700° C. at a rate of 10° C./min under the appropriate atmosphere. The sample is held at 700° C. for about 5 minutes to compensate for thermal lag. FIGS. 5 and 6 present plots of the percentage of weight of the sample retained during the heating and derivative plots of the same.

In FIG. 7 (21% oxygen), the extrudate looses a total of about 6% of the original sample mass. The largest change in mass occurs from about 150° C. to about 299° C. and accounts for a loss of about 3.1% of the original sample mass.

In FIG. 8 (10% hydrogen), the extrudate looses a total of about 28% of the original sample mass. The largest change in mass occurs from about 150° C. to about 307° C. and accounts for a loss of about 24% of the original sample mass. A maximum rate of mass loss occurs at about 281° C.

Conversion of BDO to GLB

Conversion of BDO to GLB is done in the gas phase at elevated temperature and pressure. BDO is supplied as a liquid and is vaporized prior to coming into contact with the catalyst. In one embodiment, the temperature is from about 150 to about 300° C. In another embodiment, the temperature is from about 175 to about 275° C. In yet another embodiment, the temperature is from about 185 to about 250° C. In one embodiment, the conversion of BDO to GLB is performed by contacting the inventive catalyst with either neat BDO or a mixture containing BDO in the gas or liquid phase. In another embodiment, the conversion of BDO to GLB is performed by passing neat BDO or a mixture of BDO in the gas or liquid phase at a constant or variable rate.

Similarly, the inventive catalyst can perform over a range of pressure. In one embodiment, the pressure is from about 10 to about 150 psig. In one embodiment, the pressure is from about 20 to about 200 psig. In yet another embodiment, the pressure is from about 30 to about 90 psig. The rate of BDO supplied to the catalyst can be described in terms of liquid hourly space velocity, which is defined as the mass of BDO supplied per unit mass of catalyst per hour. In one embodiment, LHSV is from about 0.1 to about 3 $hr^{-1}$. In another embodiment, LHSV is from about 0.2 to about 2 $hr^{-1}$. In yet another embodiment, LHSV is from about 0.4 to about 1.5 $hr^{-1}$.

The conversion of BDO to GLB is a dehydrogenation reaction that produces one mole of GLB and two moles of hydrogen gas per mole of BDO. However, competing side reactions are also catalyzed at low rates. The product stream may contain in addition to GLB, tetrahydrofuran (THF), water, acetal, butanol, and butyric acid among other components. In one embodiment, the conversion of BDO to GLB is over about 90%. In another embodiment, the conversion of BDO to GLB is over about 95%. In yet another embodiment, the conversion of BDO to GLB is over about 99%.

The dehydrogenation reaction of BDO to GLB does not require hydrogen to proceed. Nevertheless, hydrogen is typically included in the gas phase passed over the catalyst in order to keep metal sites in the catalyst reduced. The rate of hydrogen supplied can be described in terms of gas hourly space velocity (GHSV), which is mass of hydrogen per unit mass of catalyst per hour. In one embodiment, GHSV for hydrogen gas is from about 500 to about 2500 $hr^{-1}$. In another embodiment, GHSV for hydrogen gas is from about 750 to about 2000 hr$^{-1}$. In yet another embodiment, GHSV for hydrogen gas is from about 1000 to 1500 hr$^{-1}$.

Comparative Catalyst

A comparative catalyst was prepared in order to highlight the superior qualities of the inventive catalyst. The comparative catalyst is a CuO catalyst of a type that is well-known in the art. The CuO is placed on a support made from pumice and has a final composition of about 15% CuO, with a bulk density of about 0.6 g/ml. The comparative catalyst is provided as granules with a 4×20 mesh.

Longevity and Deactivation Rate of the Inventive Catalyst

The deactivation over time for both the comparative catalyst and Example 1 of the inventive catalyst are shown in Tables 3 and 4, respectively. The effectiveness of the catalyst is shown by the observed reaction rate constant ($k_{obs}$). The rate constant is calculated from the LHSV of BDO addition and the percentage of BDO converted by the catalyst as shown in Equation I.

$$k_{obs} = LHSV \times \ln\left(\frac{100}{100 - BDO\ \%_{conversion}}\right) \quad (I)$$

The observed rate constant will increase as the LHSV of supplied BDO increase; however, a catalyst has an intrinsic maximum rate for which reactant can be converted to product. Therefore, as LHSV for supplied BDO increases, a point will be reach where the percentage of BDO converted will decrease, referred to as the saturation rate. The observed rate constant will decrease as LHSV increases past the catalyst's intrinsic saturation rate.

Further, the observed rate constant decreases over time due to catalyst deactivation, referred to as the deactivation rate. The deactivation rate can be observed as a decrease in observed catalytic constant over time while reaction conditions are maintained as constant as possible.

TABLE 3

Comparative Catalyst Kinetics of BDO to GBL Conversion with Varying Hours of service

| Conditions | | | | |
|---|---|---|---|---|
| Hours of Service | 23 | 47 | 71 | 193 |
| Temperature Avg., C. | 200 | 200 | 230 | 200 |
| Pressure, Psig | 18 | 19 | 19 | 16 |
| LHSV, 1/hr | 0.48 | 0.48 | 0.48 | 0.47 |
| Products | | | | |
| BDO Conversion, % | 99.5 | 99.5 | 99.8 | 96.3 |
| GBL, % | 98.9 | 99.4 | 99.3 | 99.6 |
| THF, % | 0.03 | 0.04 | 0.03 | 0.04 |
| Butanol, % | 0.03 | 0.03 | 0.04 | 0.02 |
| Reaction Rate Constant Obs., 1/hr | 2.54 | 2.56 | 3.04 | 1.56 |

TABLE 4

Inventive Catalyst (Example 1) Kinetics of BDO to GBL Conversion with Varying Hours of service

| Conditions | | | | |
|---|---|---|---|---|
| Hours of Service | 24 | 44 | 119 | 311 |
| Temperature Avg., C. | 200 | 200 | 230 | 200 |
| Pressure, Psig | 18 | 19 | 19 | 21 |
| LHSV, 1/hr | 0.53 | 0.52 | 0.48 | 0.51 |
| Products | | | | |
| BDO Conversion, % | 99.7 | 99.7 | 99.9 | 99.6 |
| GBL, % | 99.4 | 98.8 | 95.9 | 98.9 |
| THF, % | 0.03 | 0.63 | 1.59 | 0.52 |
| Butanol, % | 0.13 | 0.14 | 1.2 | 0.14 |
| Reaction Rate Constant Obs., 1/hr | 3.02 | 2.95 | 3.4 | 2.85 |

As shown in Table 3, the observed rate constant for the comparative catalyst decreases from 2.54 hr$^{-1}$ at 24 hours to 1.56 hr$^{-1}$ at 193 hours, a change of 38.6% or a deactivation rate of about 0.22% per hour. By contrast, the inventive catalyst deactivates at a surprisingly slower rate. As shown in Table 4, the observed rate constant for the inventive catalyst decreases from 3.02 hr$^{-1}$ at 24 hours to 2.85 hr$^{-1}$ at 311 hours, a change of only about 5.6% or a deactivation rate of only 0.02% per hour.

Those skilled in the art will readily understand that the above described deactivation rate is only an example based on an embodiment of the inventive catalysts. Other embodiments of the inventive catalyst can have a deactivation rate that varies from the described example. In one embodiment, the deactivation rate of the catalyst is less than about 0.1% per hour. In another embodiment, the deactivation rate of the catalyst is less than about 0.05% per hour. In yet another embodiment, the deactivation rate of the catalyst is less than about 0.02% per hour. In still yet another embodiment, the deactivation rate of the catalyst is from about 0.015 to 0.025% per hour.

Catalytic Throughput of the Inventive Catalyst

As shown in Tables 3 and 4, the inventive catalyst has a high observed kinetic constant at all time points relative to the comparative catalyst. At 24 hours of service, the inventive catalyst has an observed rate constant of 3.02 hr$^{-1}$ compared to 2.54 hr$^{-1}$ for the comparative catalyst. This difference indicates an enhanced ability to support catalysis of BDO to GLB by the inventive catalyst. As shown in Tables 5 and 6, below, the saturation point for LHSV of BDO for the inventive catalyst is greatly increased. Therefore, the inventive catalyst can achieve greater observed reaction rate constants and greater throughput of BDO to GBL while maintaining a high amount of conversion.

TABLE 5

Comparative Catalyst Kinetics of BDO to GBL Conversion with Varying LHSV

| Conditions | | | |
|---|---|---|---|
| Hours of Service | 23 | 124 | 148 |
| Temperature Avg., C. | 200 | 200 | 200 |
| Pressure, Psig | 18 | 15 | 16 |
| LHSV, 1/hr | 0.48 | 0.97 | 0.3 |
| Products | | | |
| BDO Conversion, % | 99.5 | 83 | 97.6 |
| GBL, % | 98.9 | 99 | 99.6 |
| THF, % | 0.03 | 0.1 | 0.04 |
| Butanol, % | 0.03 | 0.02 | 0.02 |
| Reaction Rate Constant Obs., 1/hr | 2.54 | 1.71 | 1.11 |

TABLE 6

Inventive Catalyst (Example 1) Kinetics of BDO to GBL Conversion with Varying Hours of service

| Conditions | | | |
|---|---|---|---|
| Hours of Service | 24 | 167 | 212 |
| Temperature Avg., C. | 200 | 199 | 199 |
| Pressure, Psig | 18 | 23 | 21 |
| LHSV, 1/hr | 0.52 | 0.95 | 1.44 |
| Products | | | |
| BDO Conversion, % | 99.7 | 99.6 | 99.66 |
| GBL, % | 99.4 | 99.3 | 99.27 |
| THF, % | 0.03 | 0.17 | 0.38 |
| Butanol, % | 0.13 | 0.08 | 0.04 |
| Reaction Rate Constant Obs., 1/hr | 3.02 | 5.25 | 8.18 |

As shown in Table 5 for the comparative catalyst, the BDO conversion amount drops greatly (to 83%) when the LHSV for BDO is raised to 0.97 hr$^{-1}$. When the LHSV is dropped (to 0.30 hr$^{-1}$) at a later time, the BDO conversion amount recovers to above 97%. It is known that the saturation point for the comparative catalyst is about 0.5 hr$^{-1}$ for LHSV of BDO.

Referring to Table 6, the inventive catalyst does not exhibit any drop off in BDO conversion amount as LHSV of BDO is increased up to 1.44 hr$^{-1}$. As a consequence, a much higher throughput and observed catalytic rate constant can be achieved using the inventive catalyst. That is, the inventive catalyst can accommodate greatly increased rates of throughput (as measured by LHSV of supplied reactant) without any significant decrease in conversion amount.

Additional kinetic information for the inventive catalyst is shown in Table 7 below. Remarkably, it can be seen that half the volume of the inventive catalyst (and approximately half the weight) can accommodate approximately the same throughput as the comparative catalyst, about 20 g/hr of BDO, while maintaining a conversion rate above 99%.

Those skilled in the art will readily understand that the above described catalytic throughput is only an example based on an embodiment of the inventive catalysts. Other embodiments of the inventive catalyst can have a catalytic throughput that varies from the described example. In one embodiment, the catalyst can accommodate a LHSV of BDO from about 0.75 to about 2 hr$^{-1}$ while maintaining a BDO conversion amount of about 95% or more. In another embodiment, the catalyst can accommodate a LHSV of BDO from about 1 to about 2 hr$^{-1}$ while maintaining a BDO conversion amount of about 95% or more. In yet another embodiment, the catalyst can accommodate a LHSV of BDO from about 1 to about 2 hr$^{-1}$ while maintaining a BDO conversion amount of about 98% or more. In still yet another embodiment, the catalyst can accommodate a LHSV of BDO from about 0.75 to about 1 hr$^{-1}$ while maintaining a BDO conversion amount of about 99% or more.

TABLE 7

Throughput of BDO (g/hr) for Inventive Catalyst Relative to Comparative Catalyst

| | Comparative | Inventive (Ex. 1) | | | | Inventive (Ex. 1) | | |
|---|---|---|---|---|---|---|---|---|
| Catalyst | | | | | | | | |
| catalyst volume, ml | 40 | 40 | | | | 20 | | |
| catalyst weight, g | 23 | 29.9 | | | | 14.8 | | |
| Conditions | | | | | | | | |
| Temperature Avg., C. | 200 | 200 | 230 | 199 | 200 | 200 | 229 | 199 |
| Pressure, Psig | 19 | 19 | 19 | 23 | 22 | 15 | 16 | 17 |
| BDO Rate, g/hr | 20 | 21.9 | 20.1 | 39.8 | 81.2 | 20.6 | 20.4 | 40.1 |
| LHSV, 1/hr | 0.48 | 0.52 | 0.48 | 0.95 | 1.93 | 0.98 | 0.97 | 1.91 |
| Products | | | | | | | | |
| BDO Conversion, % | 99.5 | 99.7 | 99.9 | 99.6 | 99.4 | 99.5 | 99.9 | 95.7 |
| GBL, % | 98.9 | 98.8 | 95.9 | 99.3 | 98.8 | 98.9 | 97.8 | 98.8 |
| THF, % | 0.03 | 0.63 | 1.59 | 0.17 | 0.47 | 0.59 | 1.02 | 0.38 |
| Butanol, % | 0.03 | 0.14 | 1.17 | 8 | 0.04 | 0.06 | 0.55 | 0.03 |
| Reaction Rate Constant Obs., 1/hr | 2.54 | 2.56 | 3.4 | 5.24 | 9.94 | 5.19 | 6.41 | 6.01 |

With respect to any figure or numerical range for a given characteristic, a figure or a parameter from one range may be combined with another figure or a parameter from a different range for the same characteristic to generate a numerical range.

While the inventive catalyst compositions disclosed herein are presented for their usefulness in the catalytic conversion of BDO to GBL, those skilled in the art will readily recognize that the disclosed inventive catalytic composition can be useful for other dehydrogenation reactions. Further, the disclosed inventive catalytic composition can be potentially applied to other catalytic processes, other than dehydrogenation, where CuO based catalysts have demonstrated utility.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A catalytic composition for converting 1,4-butanediol to γ-butyrolactone comprising from about 35% to about 75% by weight of Cu, from about 15% to about 35% by weight of Al, and from about 5% to about 25% by weight of Mn, wherein the catalytic composition has two or more crystalline phases and has an x-ray diffraction pattern with peaks at the following 2-theta values when measured using Cu Kα radiation: 18.5° and 63.4°.

2. The catalytic composition of claim 1, wherein the catalytic composition does not contain an inert support phase.

3. The catalytic composition of claim 1, having an x-ray diffraction pattern with peaks at the following 2-theta values when measured using Cu Kα radiation: 18.5°, 57.7° and 63.4°.

4. The catalytic composition of claim 1, wherein the bulk density is from about 0.4 to about 0.8 g/mL.

5. The catalytic composition of claim 1 wherein, the catalytic composition comprises from about 40% to about 65% by weight of Cu, from about 20% to about 35% by weight of Al, and from about 10% to about 20% by weight of Mn and having an x-ray diffraction pattern as shown in FIG. 1.

6. A method for converting 1,4-butanediol to γ-butyrolactone, comprising:
contacting a catalytic composition of comprising from about 35% to about 75% by weight of Cu, from about 15% to about 35% by weight of Al, and from about 5% to about 25% by weight of Mn, wherein the catalytic composition has two or more crystalline phases and has an x-ray diffraction pattern with peaks at the following 2-theta values when measured using Cu Kα radiation: 18.5° and 63.4°, with 1,4-butanediol; and recovering γ-butyrolactone.

7. The method of claim 6, wherein 1,4-butanediol is contacted in the gas phase at a pressure from about 20 to about 200 psig and a temperature from about 150 to about 300° C.

8. The method of claim 6, wherein at least about 90% of 1,4-butanediol is converted to γ-butyrolactone.

9. The method of claim 6, further comprising supplying 1,4-butanediol in a liquid phase and vaporizing the liquid 1,4-butanediol prior to contacting the 1,4-butanediol with the catalytic composition, wherein the liquid 1,4-butanediol is supplied at a LHSV from about 0.1 to about 3 h$^{-1}$.

10. The method of claim 9, wherein the 1,4-butanediol is supplied at a LHSV from about 0.75 to about 2 h$^{-1}$ and at least about 95% of the 1,4-butanediol is converted into γ-butyrolactone.

11. The method of claim 9, wherein the 1,4-butanediol is supplied at a LHSV from about 1 to about 2 h$^{-1}$ and at least about 98% of the 1,4-butanediol is converted into γ-butyrolactone.

12. The method of claim 9, wherein the 1,4-butanediol is supplied at a LHSV from about 0.75 to about 1 h$^{-1}$ and at least about 99% of the 1,4-butanediol is converted into γ-butyrolactone.

13. The method of claim 9, wherein the method is associated with an observed kinetic rate constant that is calculated from the LHSV of supplied 1,4-butanediol and the percent of 1,4-butanediol is converted to γ-butyrolactone (BDO %$_{conversion}$) according to Formula I:

$$\text{observed kinetic rate constant} = LHSV \times \ln\left(\frac{100}{100 - BDO\ \%_{conversion}}\right) \quad (I)$$

and the change in the observed rate constant is less than about 0.1% per hour.

14. The method of claim 13, wherein the change in the observed rate constant is less than about 0.05% per hour.

15. A method for producing a copper catalyst, comprising:
co-precipitating a solid catalyst composition from solutions containing a soluble copper salt, a soluble manganese salt, and a soluble aluminum compound at a pH of about at about 6 to about 8.5; and
calcining the solid catalyst composition under air from about 400 to about 700° C. for a time period from about 2 to about 5 hours;
wherein the solid catalyst composition comprises from about 35% to about 75% by weight of Cu, from about 15% to about 35% by weight of Al, and from about 5% to about 25% by weight of Mn;
wherein the catalytic composition has two or more crystalline phases and has an x-ray diffraction pattern with peaks at the following 2-theta values when measured using Cu Kα radiation: 18.5° and 63.4°.

16. The method of claim 15, wherein the co-precipitation is performed by adding an aqueous solution comprising copper (II) nitrate and manganese (II) nitrate, an aqueous solution comprising sodium aluminate, and an aqueous solution comprising sodium carbonate to an aqueous media at a controlled rate.

17. The method of claim 15, further comprising optionally drying the catalytic composition, adding water to the catalytic composition to form a mixture of catalytic composition plus water, mixing the mixture of catalytic composition plus water until densification occurs, and extruding the mixture of catalytic composition plus water to form a smooth extrudate before calcining the catalytic composition.

18. The method of claim 17, further comprising performing an additional calcining of the catalytic composition before mixing the catalytic composition to densification, wherein the additional calcining is performed under air from about 400 to about 700° C. for a time period from about 2 to about 5 hours.

* * * * *